United States Patent [19]

Lui et al.

[11] Patent Number: 5,523,497

[45] Date of Patent: Jun. 4, 1996

[54] PROCESS FOR PREPARING HEXAFLUOROCHLOROBUTENES

[75] Inventors: Norbert Lui, Köln; Albrecht Marhold, Leverkusen; Dietmar Bielefeldt, Ratingen, all of Germany

[73] Assignee: Bayer Aktiengesellschaft, Leverkusen, Germany

[21] Appl. No.: 325,319

[22] PCT Filed: Apr. 22, 1993

[86] PCT No.: PCT/EP93/00980

§ 371 Date: Oct. 25, 1995

§ 102(e) Date: Oct. 25, 1994

[87] PCT Pub. No.: WO93/22263

PCT Pub. Date: Nov. 11, 1993

[30] Foreign Application Priority Data

May 4, 1992 [DE] Germany ............ 42 14 739.5

[51] Int. Cl.$^6$ .................................................. C07C 17/25
[52] U.S. Cl. ........................................ 570/155; 570/153
[58] Field of Search ........................ 570/153, 155

[56] References Cited

U.S. PATENT DOCUMENTS

| 2,413,695 | 1/1947 | Downing et al. | 260/653 |
| 4,849,554 | 7/1989 | Cresswell et al. | 570/159 |
| 5,382,720 | 1/1995 | Ikawa et al. | 570/153 |

FOREIGN PATENT DOCUMENTS

| 4214739 | 11/1993 | Germany | 570/153 |
| 3022263 | 11/1993 | WIPO | 570/153 |

OTHER PUBLICATIONS

Journal of Fluorine Chemistry vol. 35, No. 1, Feb. 1987, Lausane CH, p. 204, Matae Iwasaki et al, 'Decomposition of Some Hydrogen–Bearing Halogenated Ethanes'.

*Primary Examiner*—Alan Siegel
*Attorney, Agent, or Firm*—Joseph C. Gil

[57] ABSTRACT

1,1,1,4,4,4-hexafluoro-chlorobutenes are obtained by pyrolysis of 1,1,1-trifluoro-2,2-dichloroethane. The hexafluoro-chlorobutenes obtained in this way can be converted into hexafluorobutane, a CFC substitute, by hydrogenation.

7 Claims, No Drawings

PROCESS FOR PREPARING HEXAFLUOROCHLOROBUTENES

This application is a 371 of PCT/E093/00980 filed Apr. 22, 1993. The present invention relates to a process for preparing hexafluorochlorobutenes from trifluorodichloroethane.

Hexafluorochlorobutenes are known intermediates from which hexafluorobutanes can be prepared, these now being of interest as substitutes for chlorofluorohydrocarbons (CFCs).

It is known, from U.S. Pat. No. 2,413,695, that the pyrolysis of 1,1,1-trifluoro-2-chloroethane, a monochloro compound, leads to a saturated $C_4$-compound ($C_4H_3ClF_6$).

A process has now been found for preparing 1,1,1,4,4,4-hexafluorochlorobutenes which is characterised in that 1,1,1-trifluoro-2,2-dichloroethane is pyrolysed.

The 1,1,1-trifluoro-2,2-dichloroethane required as starting material for the process according to the invention is prepared on an industrial scale and is commercially obtainable. It may optionally be used together with 1,1,1-trifluoro-2,2,2-trichloroethane.

The pyrolysis according to the invention may be performed, for example, in the temperature range 450° to 750° C. Temperatures in the range 500° to 700° C., in particular those of 550° to 650° C. are preferred.

The pressure is of no particular significance in the process according to the invention, as long as it is ensured that the starting material is in the gaseous state at the selected pyrolysis temperature. The pressure may be, for instance, 0.1 to 50 bar. The process is preferably performed at atmospheric pressure.

The pyrolysis may optionally be performed in the presence of inert gases, for instance in the presence of noble gases or nitrogen. However, the 1,1,1-trifluoro-2,2-dichloroethane is preferably heated to the pyrolysis temperature without any additives.

The pyrolysis may be performed in such a way that, for instance, 1,1,1-trifluoro-2,2-dichloroethane is passed into one or more tubes, made of inert material and arranged in parallel, and the tube or tubes is/are heated to the desired pyrolysis temperature. Suitable materials for the tubes are, for example, quartz, nickel and nickel, chromium or molybdenum steels. The tubes may have internal diameters of, for example, 10 to 50 mm. The length of the tube or tubes and the flow-rate of the gases may be matched to each other in such a way that the residence time in the region at the pyrolysis temperature is 0.1 to 120 seconds. The residence time is preferably 1 to 30 seconds.

The tube or tubes may optionally be filled with an inert particulate material, for instance with regularly or irregularly shaped pieces of quartz with an average diameter of 1 mm to half the diameter of the particular tube. Such inert particulate material can improve heat transfer from the heated wall of the tube to the gas flowing through.

The gas mixture emerging from the pyrolysis zone may be worked up, for example, by condensing it completely or partly and isolating the hexafluorochlorobutenes contained therein by distilling them out of the condensate together or separately from each other. In the case of a partial condensation of the gas mixture emerging from the pyrolysis zone, the fraction of gas mixture which is condensable above −78° C. at atmospheric pressure, preferably above 0° C., may be condensed.

The gas mixture present after the pyrolysis zone generally contains the desired products, 1,1,1,4,4,4-hexafluoro-2-chlorobutene-2 and 1,1,1,4,4,4-hexafluoro-2,3-dichlorobutene-2, which may be present, for instance, in a molar ratio in the range 35:65 to 65:35, and 1,1,1-trifluoro-2,2,2-trichloroethane, unconverted starting material, chlorine and optionally other components in small amounts.

Unconverted 1,1,1-trifluoro-2,2-dichloroethane and 1,1,1-trifluoro-2,2,2-trichloroethane may be returned to the pyrolysis according to the invention. Chlorine may be used to prepare the starting material. The hexafluorochlorobutenes obtained may together be subjected to hydrogenation to produce 1,1,1,4,4,4-hexafluorobutane, which can be used as a CFC-free blowing gas for preparing foams.

Hydrogenation of 1,1,1,4,4,4-hexafluoro-2-chlorobutene-2 and 1,1,1,4,4,4-hexafluoro-2,3-dichlorobutene-2 to give 1,1,1,4,4,4-hexafluorobutane can be performed, for example, catalytically and in the gas phase. Suitable temperatures for this hydrogenation are, for example, in the range 80° to 400° C., suitable catalysts are, for example, transition metals on supported catalysts, in particular palladium and platinum on activated carbon and lithium aluminium spinels. Suitable pressures for this hydrogenation are, for example, those between atmospheric pressure and 20 bar. A hydrogenation process of this type is described, for instance, in DE-OS 40 04 497. In principle, however, other hydrogenation processes may also be used.

The process for the preparation of 1,1,1,4,4,4-hexafluoro-chlorobutenes according to the invention requires no hydrogen and no catalysts, utilises easily accessible starting materials, yields chlorine, which is simple to separate and can be recycled, as a side product and can also be performed in a simple manner. It is extremely surprising that, in contrast with the prior art described at the beginning, according to the invention, unsaturated hexafluoro-chlorobutenes are obtainable from a dichloroethane compound by pyrolysis.

EXAMPLES

Example 1

60 g per hour of 1,1,1-trifluoro-2,2-dichloroethane were evaporated in a pre-evaporator, consisting of a 20 cm long quartz tube (internal diameter 25 mm) which was filled with particles of quartz, and heated to 100° C. Then the gas obtained in this way was then introduced to a 35 cm long quartz tube (internal diameter 25 mm) which was also filled with particles of quartz and electrically heated to 625° C. The gas emerging from the second quartz tube was condensed at 15° C. and then investigated using gas chromatography. Over the course of one hour, 50 g of a mixture were obtained which contained 40 wt. % of hexafluorochlorobutenes (approximately equal parts by weight of 1,1,1,4,4,4-hexafluoro-2-chlorobutene-2 and 1,1,1,4,4,4-hexafluoro-2,3-dichlorobutene-2), 31 wt. % of unconverted 1,1,1-trifluoro-2,2-dichloroethane and 17 wt. % of 1,1,1-trifluoro-2,2,2-trichloroethane. The 1,1,1-trifluoro-2,2-dichloroethane used had been up to 72% converted.

Hexafluorochlorobutenes, which could be hydrogenated after distillative separation to give hexafluorobutane, had been formed with a selectivity of 57%.

Example 2

The trifluorochloroethanes obtained during working up in accordance with example 1 (1,1,1-trifluoro-2,2-dichloroethane and 1,1,1-trifluoro-2,2,2-trichloroethane) were combined and made up to 60 g with fresh 1,1,1-trifluoro-2,2-dichloro-ethane. The mixture obtained in this way was pyrolysed as described in example 1 and the condensate was investigated using gas chromatography. In the course of 1 hour, 52 g of a mixture was formed which consisted of up to 37 wt. % of hexafluorochlorobutenes (46 wt. % of 1,1,1,4,4,4-hexafluoro-2-chlorobutene-2 and 54 wt. % of 1,1,1,4,4,4-hexafluoro-2,3-dichlorobutene-2).

We claim:

1. A process for preparing 1,1,1,4,4,4-hexafluorochlorobutenes, comprising pyrolyzing 1,1,1-trifluoro-2,2-dichloroethane at a temperature of from 625° to 750° C.

2. The process of claim 1, wherein a mixture of 1,1,1-trifluoro-2,2-dichloroethane and 1,1,1-trifluoro-2,2,2-trichloroethane is pyrolyzed.

3. The process of claim 1, wherein the pyrolysis is performed at pressures in the range of 0.1 to 50 bar.

4. The process of claim 1, wherein the pyrolysis is performed in tubes made of inert material.

5. The process of claim 4, wherein residence times of 0.1 to 120 seconds are maintained in the region at the pyrolysis temperature.

6. The process claim 4, wherein the tubes are filled with inert particulate materials.

7. The process of claim 1, wherein the gas mixture emerging from the pyrolysis zone is condensed and the hexafluorochlorobutenes contained therein are isolated from the condensate by distillation.

* * * * *